United States Patent
Platzek

(10) Patent No.: US 6,832,505 B2
(45) Date of Patent: Dec. 21, 2004

(54) RHEOMETER

(75) Inventor: Wolfgang Platzek, Karlsruhe (DE)

(73) Assignee: Thermo Electron (Karlsruhe) GmbH, Karlsruhe (DE)

( * ) Notice: Subject to any disclaimer, the term of this patent is extended or adjusted under 35 U.S.C. 154(b) by 0 days.

(21) Appl. No.: 10/674,556

(22) Filed: Oct. 1, 2003

(65) Prior Publication Data

US 2004/0069050 A1 Apr. 15, 2004

(30) Foreign Application Priority Data

Oct. 14, 2002 (DE) .......................................... 102 47 783

(51) Int. Cl.[7] .............................................. G01N 11/14
(52) U.S. Cl. ..................... 73/54.35; 73/54.28; 73/54.01; 73/53.01
(58) Field of Search ............................ 73/54.35, 53.01, 73/54.28, 760, 763, 781, 843

(56) References Cited

U.S. PATENT DOCUMENTS

| | | | |
|---|---|---|---|
| 3,886,789 A | * 6/1975 | Brookfield ................. | 73/54.35 |
| 5,798,454 A | * 8/1998 | Nakazeki et al. .......... | 73/54.28 |
| 6,100,618 A | * 8/2000 | Schoeb et al. ............. | 310/90.5 |
| 6,167,752 B1 | 1/2001 | Raffer | |
| 6,282,948 B1 | * 9/2001 | O'Dell et al. .............. | 73/54.28 |
| 6,640,617 B2 | * 11/2003 | Schöb et al. ............... | 73/54.01 |

FOREIGN PATENT DOCUMENTS

DE            44 36 156            3/1996

* cited by examiner

Primary Examiner—Hezron Williams
Assistant Examiner—Rodney T. Frank
(74) Attorney, Agent, or Firm—Paul Vincent

(57) ABSTRACT

A rheometer has a rotor comprising a shaft which is seated with play in a recess of a bearing block and is supported contact-free in a radial and/or axial direction by an external air cushion which acts in a bearing section. To provide for simple and inexpensive production of an air bearing having a high loading capacity, the wall of the recess in the bearing section is continuous without bore-holes, and consists of air-permeable material. The bearing air loads the side of the wall facing away from the shaft and penetrates through the wall.

11 Claims, 1 Drawing Sheet

RHEOMETER

This application claims Paris Convention priority of DE 102 47 783.3 filed Oct. 14, 2002 the complete disclosure of which is hereby incorporated by reference.

BACKGROUND OF THE INVENTION

The invention concerns a rheometer with a rotor surrounding a shaft which is seated with play in a recess of a bearing block and is supported contact-free in a radial and/or axial direction by means of an exterior air cushion acting in a bearing section.

Measurement of rheological values in a rheometer is based on the exact knowledge of the relationship between shearing strain or stress and deformation of the substance to be examined. One of the two values is predetermined and the other is measured by a measuring means. To derive the exact material properties from these values, the mechanical friction loss of the measuring means must be kept to a minimum. This is achieved in a rheometer of the mentioned type as described e.g. in U.S. Pat. No. 6,167,752 or DE 44 36 156 C1 in that a shaft of a rotor of the measuring means is supported in a radial and axial direction by air bearings. The air bearing is formed in a bearing body which has a recess with an axial through-hole and a cylindrical chamber extending substantially coaxially thereto. The shaft is inserted into the axial through-hole with play and carries an annular disk which extends perpendicularly to its axial direction and is seated with play in the cylindrical chamber.

The bearing body is penetrated by a web of very fine air channels which terminate on the surface of the through-hole facing the shaft and of the cylindrical chamber and are connected to an air supply. The pressurized air supplied from the air supply flows through the air channels and exits at their openings thereby forming, in the region of the through-hole, an air cushion surrounding and radially centering the shaft, and, in the region of the cylindrical chamber, a further air cushion axially supporting the disk and thereby the shaft.

To produce an air cushion which acts as uniformly as possible over the bearing surface, a plurality of very fine air outlet openings with small mutual separation must be formed and connected to the fine air channels. To achieve the precision required in this case, laser cutting methods are e.g. used, as a result of which the production of the bearing body is very demanding and expensive. Moreover, there is the danger that the heat from the laser beam produces melt-outs or ridges, which can prevent uniform air flow. It has also turned out that the loading capacity, i.e. the bearing force capacity of known air bearings, is limited which suggests that air bearing technology has reached its limits.

It is the underlying purpose of the invention to produce a rheometer of the above-mentioned type with an air bearing which is simple and inexpensive to produce and has a high loading capacity.

SUMMARY OF THE INVENTION

This object is achieved in accordance with the invention in a rheometer of the mentioned type in that the wall of the recess in the bearing section is continuous, without boreholes, and consists of an air-permeable material, wherein the bearing air loads the side of the wall facing away from the shaft and penetrates through the wall.

The invention is based on the underlying idea that the air channels formed through processing of the bearing block, do not terminate in the wall of the recess. The air is guided towards the wall of the recess from the outside only to such an extent that it loads the side of the wall facing away from the shaft. The air cushion which supports the shaft in an axial and/or radial direction is effected in that at least the wall of the recess is formed from an air-permeable material which is preferably sintered carbon, so-called artificial graphite, or air-permeable ceramics or porous plastic material and, in particular, foamed material. The bearing air penetrates through the wall due to its large number of pores or microchannels, thereby leading to a uniform air cushion structure. This produces a high bearing stability for the shaft in a horizontal i.e. radial direction and also in a vertical e.g. axial direction. At the same time, processing required to form the air bearing is simplified, since the bearing air must only be guided to the outer side of the wall by air channels which must not be precisely dimensioned. Very fine bores which penetrate the wall are not needed. This also safely eliminates the above-mentioned danger of producing melt-outs or ridges due to heat.

In a preferred embodiment of the invention, the shaft is borne in its radial direction, wherein the recess has a through-hole which receives the shaft with play and in which it is supported in a radial direction by a radially outer air cushion.

In a preferred embodiment of the invention, the shaft is axially supported by an air bearing in that the recess comprises a cylindrical chamber containing a disk with play which is seated on the shaft and extends substantially perpendicularly to its axial direction. The disk and the shaft are supported in both axial directions by an axial air cushion formed on both sides of the disk.

Pressurized bearing air is supplied to the side of the recess wall facing away from the shaft preferably through several air channels which are formed in the bearing block and are preferably connected to each other. In a preferred embodiment, the side of the recess wall facing away from the shaft or disk, has several annular channels separated in an axial direction of the shaft which distribute the bearing air over the periphery of the shaft thereby ensuring uniform passage or exit of bearing air on the side of the wall facing the shaft. In a preferred embodiment of the invention, the annular channels are connected via several axial channels, separated in the peripheral direction, and are preferably connected to one single common pressurized air source or air supply. The air supply may comprise one or more control valves to produce different air bearing pressures for different regions, i.e. different bearing rigidities within the air bearing.

The air supply for the air bearing formed in the cylindrical chamber which supports the disk and the shaft in its axial direction, preferably also comprises annular channels, one of which is formed on each axial side of the cylindrical chamber at a small separation from its wall such that the air from the annular channels can penetrate through the wall in an axial direction from opposing sides into the cylindrical chamber, wherein the two air flows bear the disk between them and therefore the shaft.

Further details and features of the invention can be extracted from the following description of an embodiment with reference to the drawing.

DESCRIPTION OF THE PREFERRED EMBODIMENT

Figure 1:
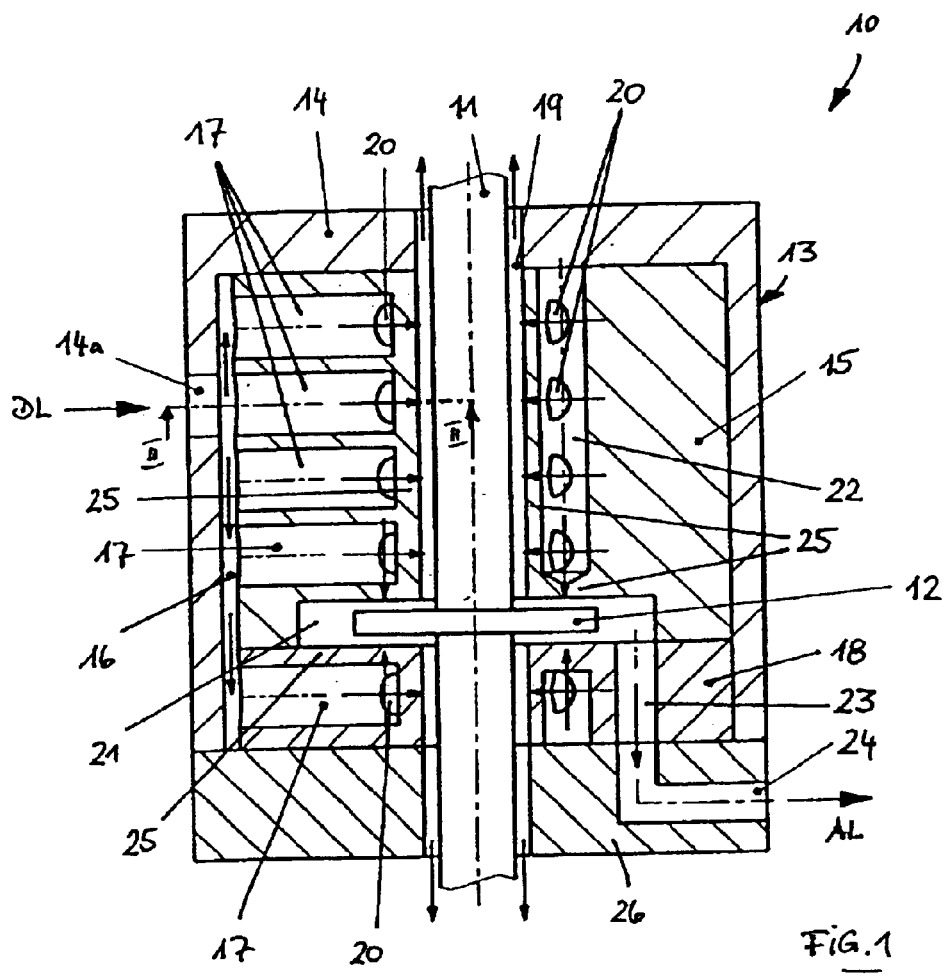
FIG. 1 shows a vertical section through a bearing of a rheometer shaft.
Figure 2:
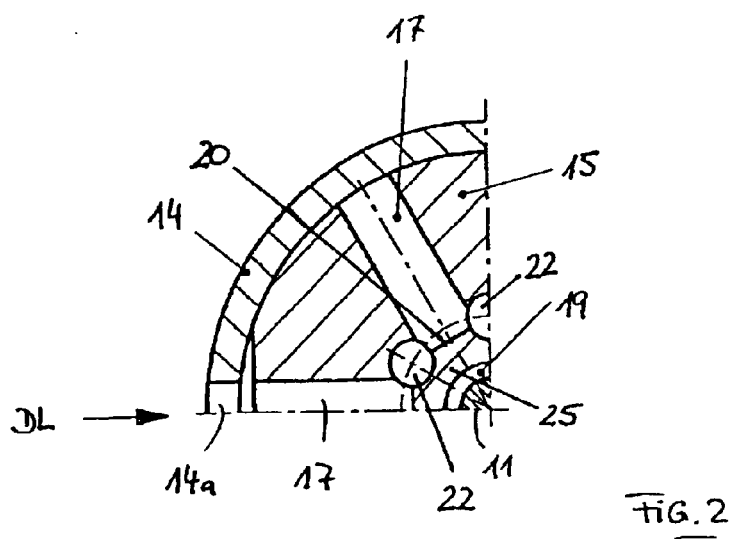
FIG. 2 shows a partial view of the section II—II of FIG. 1.

FIGS. 1 and 2 show a bearing device 10 for a shaft 11 of a rotor (not shown in detail) of a rheometer. The shaft 11 extends substantially vertically and bears a disk 12 which extends perpendicularly to its axial direction and surrounds the shaft 11 like a circular ring.

The shaft 11 is air-cushioned together with the disk 12 in a bearing block 13 in its axial and radial direction. The bearing block 13 comprises a cup-shaped housing 14 into which a first bearing part 15 and a second bearing part 18, axially bordering thereto, are inserted which substantially completely fill the inner space of the housing 14. The housing 14 is covered at its open side by a lid 26. A central through-hole 19 extends through the housing 14, the first bearing part 15, the second bearing part 18 and the lid 26, into which the shaft 11 is inserted with radial play. A central circular cylindrical chamber 21 is formed in the transition region between the first bearing part 15 and second bearing part 18 and accommodates the disk 12 of the shaft 11 with axial play. The through-hole 19 and the cylindrical chamber 21 define a recess which is delimited by a closed continuous wall 25, devoid of bore-holes.

The housing 14 has a lateral bore which serves as air supply 14a to which air can be supplied from a pressurized air source (not shown) indicated by arrow DL. An air distribution chamber 16 is formed in the region of the air supply 14a in the first bearing part 15 and in the second bearing part 18, which extends in the vertical direction and from which several air channels 17 branch off which extend substantially horizontally towards the shaft 11 and which are mutually separated in an axial direction of the shaft 11. The air channels 17 terminate on the side of the wall 25 of the recess facing away from the shaft 11. One annular channel 20, which extends in the peripheral direction, follows this inner end of each horizontal air channel 17 and completely surrounds the shaft 11 on the side of the wall 25 facing away from the shaft 11. The annular channels 20, disposed one on top of the other, are interconnected via axial channels which extend parallel to the shaft 11 and which are distributed about the periphery of the shaft 11.

One horizontal air channel 17 is disposed in the region of the cylindrical chamber 21 at each axial side of the chamber 21, each of which terminates in an associated annular channel 20. In this fashion, the bearing air accumulates on both axial sides of the cylindrical chamber 21 on the side of the wall 25 facing away from the disk 12. An exhaust air channel formed by bores 23 and 24 extends from the cylindrical chamber 21 through the second bearing part 18 and the lid 26 to the outside of the housing 14 such that the exhaust air can exit the bearing device as indicated by arrow AL.

The first bearing part 15 and the second bearing part 18 consist of an air-permeable material and, in particular, of a sintered carbon. The pressurized air introduced into the housing 14 by the air supply 14a is distributed via the air distributing chamber 16 to different horizontal air channels 17 and accumulates in the downstream annular channels 20, wherein the axial channels 22 provide air and pressure compensation between the annular channels 20. Due to the air permeability of the material of the bearing parts 15 and 18, the air may penetrate the wall 25 such that an air cushion is formed in the axial bore 19 about the shaft 11 which centers and bears the shaft 11 in the through-hole 19 and the air cushion also enters the cylindrical chamber 21 from opposite sides also in a vertical direction i.e. axial direction of the shaft 11, thereby bearing the disk 12 therebetween and bearing the shaft 11 in an axial direction. The porosity of the material of the bearing parts 15 and 18 thereby provides homogeneous flow conditions within the air cushion bearing the shaft 11 and the disk 12 without having to drill into or otherwise perforate the recess wall 25 formed by the through-hole 19 and the cylindrical chamber 21 through post-processing.

I claim:

1. A rheometer comprising:
   a bearing block having a continuous wall section, without bore-holes, made from an air-permeable material, said continuous wall section defining a recess;
   a rotor having a shaft, said shaft disposed with play in said recess of said bearing block; and
   means for applying pressurized bearing air to a side of said wall section facing away from said shaft, wherein said bearing air penetrates through said wall to form an external air cushion within said recess for supporting said shaft in a contact free, radial and/or axial direction.

2. The rheometer of claim 1, wherein said recess has a through-bore in which said shaft is supported in a radial direction by a radially outer air cushion.

3. The rheometer of claim 1, wherein said rotor comprises a disk seated on said shaft, said disk extending in a substantially perpendicular direction relative to an axial extension of said shaft, said recess having a cylindrical chamber in which said disk is disposed with play and in which said disk and said shaft are supported in an axial direction by an axial air cushion.

4. The rheometer of claim 1, wherein said bearing block has several air channels formed therein, to guide said bearing air to a side of said wall of said recess facing away from said shaft.

5. The rheometer of claim 3, wherein said bearing block has several air channels formed therein to guide said bearing air to a side of said wall of said recess facing away from said disk.

6. The rheometer of claim 1, wherein several axially spaced annular channels are formed on a side of said wall of said recess facing away from said shaft.

7. The rheometer of claim 3, wherein several axially spaced annular channels are formed on a side of said wall of said recess facing away from said disk.

8. The rheometer of claim 6, wherein said annular channels are connected via several axial channels, separated in a peripheral direction.

9. The rheometer of claim 7, wherein said annular channels are connected via several axial channels, separated in a peripheral direction.

10. The rheometer of claim 4, wherein said air channels are connected to a common air supply.

11. The rheometer of claim 1, wherein said air-permeable material is one of sintered carbon, artificial graphite and ceramic.

* * * * *